United States Patent [19]

Karow, Jr.

[11] 4,262,494

[45] Apr. 21, 1981

[54] PORTABLE DEVICE FOR CRYOPRESERVATION, TRANSPORTATION AND TEMPORARY CRYOGENIC STORAGE OF SEMEN AND OTHER SIMILAR TISSUE

[76] Inventor: Armand M. Karow, Jr., 3052 Westwood Ct., Augusta, Ga. 30909

[21] Appl. No.: 117,009

[22] Filed: Jan. 30, 1980

[51] Int. Cl.³ .............................................. F25D 3/12
[52] U.S. Cl. ...................................... 62/384; 62/457; 62/514 R
[58] Field of Search ....................... 62/62, 64, 78, 384, 62/457, 514 R

[56] References Cited

U.S. PATENT DOCUMENTS

| | | | |
|---|---|---|---|
| 3,151,760 | 10/1964 | Cowley et al. | 62/457 |
| 3,303,667 | 2/1967 | Perkins | 62/457 |
| 3,810,367 | 5/1974 | Peterson | 62/64 |
| 3,940,249 | 2/1976 | McClurg | 62/457 |
| 4,199,022 | 4/1980 | Senkan et al. | 62/78 |

*Primary Examiner*—Ronald C. Capossela
*Attorney, Agent, or Firm*—Earl D. Harris; William R. Alford

[57] ABSTRACT

This invention relates to an apparatus for freezing, transporting, and temporary storage of animal and/or human tissue (such as semen) for use in veterinary or medical practice (such as artificial insemination), where the collection is performed under field conditions not in the geographic vicinity of a storage facility and transportation is accomplished by public carrier to a storage facility at an extended distance.

8 Claims, 3 Drawing Figures

PORTABLE DEVICE FOR CRYOPRESERVATION, TRANSPORTATION AND TEMPORARY CRYOGENIC STORAGE OF SEMEN AND OTHER SIMILAR TISSUE

BACKGROUND OF THE INVENTION

In many situations it is desirable to collect semen and other like cryogenically storable tissue (such as blood, bone marrow, or other living tissue suspended in a liquid medium) in a "field" situation where immediate cryogenic storage facilities are not readily available. However, because such tissue dies or loses it effectiveness and efficiency if not frozen for storage in a relatively brief period of time after donation, the donor (whether animal or human) is usually required to be in the same geographic vicinity of the storage facility to facilitate collection and initial freeze-processing of the tissue. Although many advances have been made in the freezing, storage and thawing of such tissue which have met with relatively high success, the art has been hampered by the lack of adequate portable freeze-processing facilities or apparatus which would allow for initial freeze-processing (hereinafter called cryopreservation) and for economic, safe transportation of the same to permanent storage facilities.

Since freezing usually kills living cells, the cells must first be treated with a suitable cryoprotectant chemical, cooled at a specific controlled rate of temperature decrease relative to time, maintained at cryogenic temperature until utilization is desired, and thawed at specific, controlled rate temperature increase. The rate of cooling required to maintain the viability of cells and tissue is dependent, in part, upon the nature of the cryoprotectant chemical, such as glycerol or dimethyl sulfoxide, used and the type of cells or tissue being frozen.

After treatment with the cryoprotectant chemical, the tissue is inserted into elongated plastic tubes or straws, which themselves are of such decreased diameter, size and mass as to expose more surface area of the tissue to the freezing medium and allow relative uniform freezing of the tissue. Although freezing and storage is at low temperatures and must be accomplished at controlled rates, care must be taken not to allow a rate so rapid or so slow as to destroy the tissue and its effectiveness and efficiency. It has been determined by empirical studies that an appropriate rate of freezing can be accomplished by suspending the tissue at predetermined distances (relative to the tissue, cryoprotectant chemical, size or diameter of storage straws, etc.) from the surface of liquid nitrogen with an ambient temperature of 20° C. Temporary storage for transportation purposes has previously been accomplished by use of a Dewar flask or other such container in conjunction with low temperature liquid gases such as liquid nitrogen; however, safety hazards in handling and spillage of the liquid gas or freezing agent during transportation has presented serious drawbacks in such means.

It has been found that controlled rates of freezing can also be accomplished by use of low-temperature solid freezing agent having temperatures of −75° C. or lower, such as frozen carbon dioxide, in a similar manner as is used with liquid gas freezing agents. The subject invention is a portable apparatus which utilizes frozen solid freezing agents and allows controlled rate-freezing by varying the amount and quality of insulation material between the tissue and the freezing agents depending parameters such as tissue preserved and the cryoprotectant used.

SUMMARY OF THE INVENTION

The invention is a system of three containers for the freezing and short-term storage of semen and other similar tissue at critically low cryogenic temperatures after collection and during conventional transportation to a permanent storage facility. In the apparatus of the present invention, tissue straws or tubes, containing the treated tissue, are secured inside a hollow canister of heat conducting material in such a manner as to prevent the straws from being in contact with the interior walls of the canister; the canister is filled with an insulating medium and are secured in an insulated metal box; the insulated box is itself surrounded on all sides with the solid freezing medium in a shipping container. Both the insulating medium in the canister and the insulation of the metal box may be selected for quality and quantity to attain the desired rate of temperature change, but should be of a gas (e.g. air) or liquid which does not change physical form (liquify or freeze) in the temperature range to which it will be subjected and which does not chemically interact with the invention components, including the semen straws. The semen straws must be secured within the canister in a manner to prevent them from being in contact with any heat conducting materials other than the insulating medium. The insulating medium surrounding the straws, as cooled by the canister walls, provides the controlled-rate of cooling and freezing for the tissue. By varying the quantity and quality of the insulating medium the rate can itself be varied.

The canisters are secured in a metal box for stability in transportation. The insulation in such box, and between its interior walls and the canisters, provides a further control over the cooling and freezing rate in the same mannner as does the insulating medium inside the canister.

An important advantage of this inventive system is that commerical freezing media, such as frozen carbon dioxide, are readily available, which, when use in this system, are sufficient to freeze and store tissue for sufficient periods to allow transportation by conventional methods to distant permanent storage facilities.

A further advantage is that the cooling-freezing rate of the tissue can be infinitely adjusted to correspond to desired or required rate by varying a number of parameters, such as: quantity or quality of the insulating medium in the canister or the insulation in the metal box; the diameter, size and/or mass of the straw; and the type of ccryoprotectant chemical.

A further advantage is that the invention allows use under field conditions by medical technicians who have not been specifically trained in cryogenic storage and freezing procedures by providing a simple, convenient method of packaging where the rate of cooling and freezing is predetermined by adjustments in certain parameters in the assembly of the invention prior to collection of the tissue.

A further advantage is that the invention eliminates the use of freezing agent such as liquid nitrogen that present safety hazards and are difficult to contain during transportation by conventional means.

DESCRIPTION OF INVENTION

Figure 1:
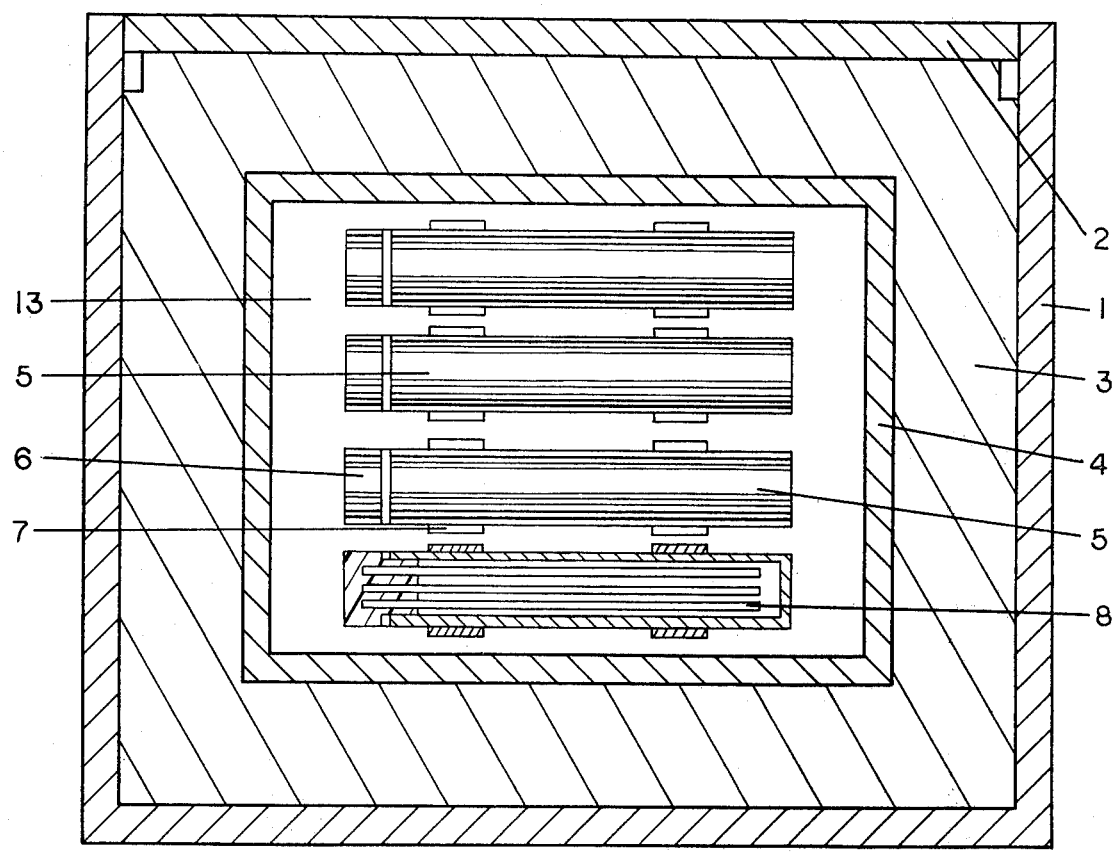
FIG. 1 is a cross-sectional view showing the tissue straws inside a canister, the canisters affixed to a box, and the box surrounded by a freezing agent contained in an insulated shipping container.
Figure 2:
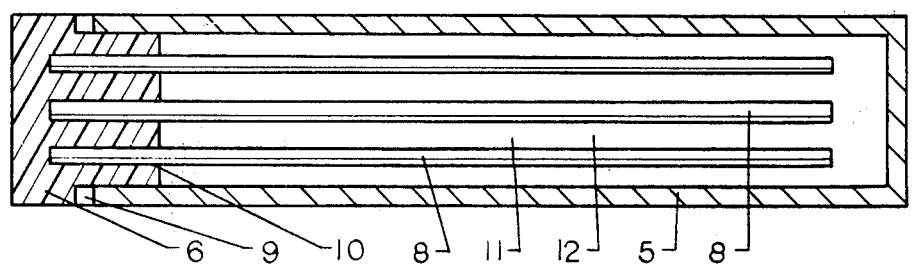
FIG. 2 is a cross-sectional view of the canister with a stopper containing the tissue straws in receptacles and sealed with an O-ring.
Figure 3:
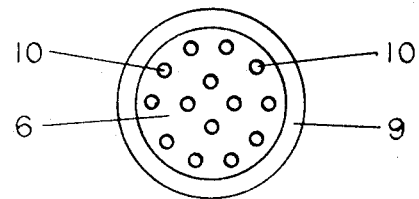
FIG. 3 is a bottom view of the canister stopper showing a plurality of receptacles and the O-ring sealer.

Referring first to FIG. 1, the invention includes a plurality of canisters 5, fitted with stoppers 6, and held by fastners 7 or other means of attaching in a heat conducting box 4. The box 4 is contained in an insulated shipping container 1 and surrounded by a solid freezing agent, such as frozen carbon dioxide. The insulated shipping container 1 is fitted with a closure 2 which allows for the escaping vapors from the freezing agent 3.

Each canister 5 is made of heat conductive material, is hollow, and has an open end and a closed end forming a chamber 11. Each canister 5 is fitted at the open end with a stopper 6 made of a non-heat conducting material, such as Teflon, into which tissue or semen straws made of a suitable plastic, as is known in the art, are inserted. An O-ring 9, made of a flexible insulating material which does not become brittle when subjected to low temperatures, such as neoprene, is positively affixed to the stopper to insulate the stopper 6 from the canister 5, and is of a suitable size to form an airtight chamber 11 within the canister 5, to seal the chamber 11 from the outside atmosphere.

The stopper 6 has a plurality of elongated, parallel receptacles 10 constructed and arranged to receive tissue straws 8. The receptacles 10 are parallel to the sides of the stopper 6 and receive tissue straws 8 in a manner to prevent such tissue straws 8 from contacting the interior walls of the canister 5 or one another when the stopper 6 is inserted in the open end of said canister 5.

The collected tissue is inserted into the tissue straws 8, which are, in turn, placed in the elongated receptacles 10 in the stopper 6. The stopper 6 is inserted into the open top of the canister 5 in a manner that the tissue straws 8 are contained in the chamber 11 within the canister 5 but not in contact with the interior canister walls. A suitable insulating medium 12, such as air, is placed inside the chamber 11 and surrounding the tissue straws 8. The O-ring 9, positively affixed to the stopper 6, seals the chamber 11 from the outside atmosphere.

The canister 6 is then attached to box 4 by means of any suitable fastner 7, such as clips; and after insulation 13 is placed in the box 4, the box 4 is, in turn placed inside the insulated container 1, and is surrounded by the freezing agent 3, such as dry ice. A closure 2 is loosely placed over the open end of the insulated shipping container 2, to hold the contents, within the said container 2 but loose enough to allow vapors from the freezing agent 3 to escape, preventing excessive pressure.

What is claimed:

1. A device for cryogenically freezing, storing and transporting live tissue of living cells suspended in liquid medium comprising, in combination:
   a. A stopper of a suitable non-heat conducting material, said stopper being fitted on its bottom end with a plurality of receptacles for the insertion and holding of tissue straws,
   b. an elongated tubular canister of uniform cross-section, said canister being sealed at one end and open at the other end for the reception of said tissue straws and stopper into a chamber within said canister,
   c. a means for maintaining said tissue straws substantially parallel and a positive distance from the interior walls of said chamber,
   d. a first insulating medium filling said chamber,
   e. a means for sealing said stopper to said canister,
   f. a box for containing a plurality of said canisters,
   g. a means for attaching said canisters to said box,
   h. a second insulating medium filling said box,
   i. an insulated shipping container fitted with a ventilated top,
   j. a freezing medium to cryogenically freeze said tissue surrounding said box and contained within said container.

2. The device of claim 1 wherein said stopper is made of Teflon.

3. The device of claim 1 wherein said means for maintaining said tissue straws parallel and a positive distance from the interior walls of said chamber is a plurality of parallel receptacles placed in the bottom end of said stopper.

4. The device of claim 1 wherein said first insulating medium is air.

5. The device of claim 1 wherein said means of sealing said stopper to said canister is an O-ring.

6. The device of claim 1 wherein said second insulating medium is air.

7. The device of claim 1 wherein said means for attaching said canisters to said box are clips.

8. The device of claim 1 wherein said freezing medium is frozen carbon dioxide.

* * * * *